United States Patent [19]

Mukai et al.

[11] Patent Number: 4,990,634

[45] Date of Patent: Feb. 5, 1991

[54] NOVEL TETRACYANOANTHRAQUINODIMETHANE DERIVATIVES AND PROCESS FOR PRODUCING SAME

[75] Inventors: Toshio Mukai, 2-1-2, Tsunogoro, Sendai-shi, Miyagi; Yoshiro Yamashita; Takanori Suzuki, both of Miyagi; Yutaka Akasaki, Kanagawa; Katsuhiro Sato, Kanagawa; Naoya Yabuuchi, Kanagawa; Hiroyuki Tanaka, Kanagawa; Katsumi Nukada, Kanagawa, all of Japan

[73] Assignees: Fuji Xerox Co., Ltd., Tokyo; Toshio Mukai, Miyagi, both of Japan

[21] Appl. No.: 95,797

[22] Filed: Sep. 14, 1987

[30] Foreign Application Priority Data

Sep. 12, 1986 [JP] Japan .................. 61-214062
Sep. 12, 1986 [JP] Japan .................. 61-214063
Sep. 24, 1986 [JP] Japan .................. 61-223766
Sep. 24, 1986 [JP] Japan .................. 61-223767
Oct. 22, 1986 [JP] Japan .................. 61-249541

[51] Int. Cl.$^5$ ............... C07C 50/16; C07C 50/06; C07C 97/18
[52] U.S. Cl. ................... 552/210; 552/503
[58] Field of Search ........... 260/376, 369, 378, 384, 260/377, 381; 552/210, 303

[56] References Cited

U.S. PATENT DOCUMENTS 4,500,459  2/1985  Hotta et al. .............. 260/346 N
4,510,089  4/1985  Hotta et al. .............. 260/396 N
4,606,861  8/1986  Ona et al. ................ 260/396 N Primary Examiner—Glennon H. Hollrah
Assistant Examiner—Raymond Covington
Attorney, Agent, or Firm—Sughrue, Mion, Zinn, Macpeak & Seas

[57] ABSTRACT

A novel tetracyanoanthraquinodimethane derivative and a process for producing it are disclosed, the tetracyanoanthraquinodimethane derivative being represented by formula:

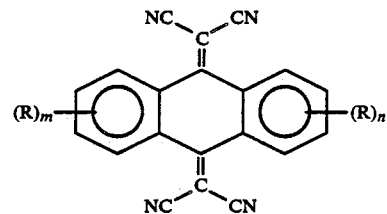

wherein R, m, and n are as defined in the specification. A solid charge transfer complex of the tetracyanoanthraquinodimethane derivative with an electron donating compound and a process for producing it are also disclosed.

3 Claims, 4 Drawing Sheets

TETRACYANOANTHRAQUINODIMETHANE DERIVATIVES AND PROCESS FOR PRODUCING SAME

FIELD OF THE INVENTION

This invention relates to a novel tetracyanoanthraquinodimethane derivative excellent in electron transporting properties and a process for producing the same.

BACKGROUND OF THE INVENTION

In the field of electrophotography, attempts have recently been made to utilize organic materials for electrophotographic photoreceptors. The organic photoreceptor is composed of a combination of a material capable of generating a charge (hereinafter referred to as "charge generating material") and a material capable of transporting a charge (hereinafter referred to as "charge transport material"), in which a charge generating layer containing a charge generating material and a charge transport layer containing a charge transport material are laminated on a support to form a photosensitive layer, or a photosensitive layer having a charge generating material dispersed in a charge transport material is formed on a support, as described, for example, in U.S. Pat. Nos. 4,559,286, 4,555,463, and 4,552,822.

The charge to be transported includes positive holes and electrons. Most of the conventionally proposed charge transport materials are capable of transporting positive holes only, as exemplified by pyrazolines, hydrazones, and the like, while there is only a mixture of polyvinylcarbazole (PVK) and trinitrofluorenone (TNF) known as a practically employable charge transport material capable of transporting electrons. Since the conventional photoreceptors using positive hole-transport materials are composed of a support, a charge generating layer, and a charge transport layer in this order, they should be charged negatively. Such negatively working photoreceptors are unavoidably susceptible to chemical denaturation due to negatively charged ozone and, therefore, they have considerably poor printing durability as compared with inorganic photoreceptors containing amorphous selenium, amorphous silicon or other inorganic materials. Besides, they fail to exhibit capability of being charged both positively and negatively, i.e., bipolarity. From these considerations, it has been demanded to develop an electrophotographic photoreceptor capable of transporting electrons, and more desirably a bipolar photoreceptor.

Tetracyanoanthraquinodimethane (hereinafter abbreviated as "TCNAQ") and its derivatives are known as organic compounds chargeable to both polarities as described in Japanese Patent Application (OPI) Nos. 149259/82, 10554/83, and 55450/83 (the term "OPI" as used herein means "unexamined published Japanese patent application").

The TCNAQ derivatives have a basic skeleton represented by formula:

to which various substitutents are bonded.

These compounds are useful as organic electronic materials, such as organic conductors, thermistor materials, etc., but have a disadvantage of low electrical conductivity.

The TCNAQ derivatives have been conventionally prepared through a series of steps as shown below as disclosed in Japanese Patent Application (OPI) No. 10554/83:

According to the above-illustrated process, a number of steps are involved, the reaction time required is long, the operation is complicated, and the yield is low. In addition, since the resulting product has a low purity, it produces many trap sites, when used as a charge transport material of electrophotographic photoreceptors, resulting in the failure of attaining a low residual potential and suppressing changes with time.

SUMMARY OF THE INVENTION

Accordingly, one object of this invention is to provide a tetracyanoanthraquinodimethane derivative which is excellent in electron transporting properties, and capable of transporting both electrons and positive holes.

Another object of this invention is to provide a process for producing a tetracyanoanthraquinodimethane derivative useful as a charge transport material through easy operation in a reduced time at a high yield and a high purity.

A further object of this invention is to provide a tetracyanoanthraquinodimethane-based charge transfer complex having a high electrical conductivity, and a process for producing the charge transfer complex.

That is, the present invention is a tetracyanoanthraquinodimethane derivative represented by formula (I)

wherein R represents a halogen atom, a cyano group, a nitro group, an alkyl group, an alkoxycarbonyl group, or a dialkylamino group, and m and n each represents 0, 1 or 2 and m+n is 2, provided that n is 1 and m+n is 1 or 2 when R is a dialkylamino group.

The TCNAQ derivatives represented by formula (I) can be produced by subjecting malononitrile represented by formula (II):

and an anthraquinone derivative represented by formula (III):

to Knoevenagel condensation reaction in the presence of titanium tetrachloride and a tertiary organic base.

DETAILED DESCRIPTION OF THE INVENTION

In formula (I), R represents a halogen atom such as a chlorine atom and a bromine atom; a cyano group; a nitro group; an alkyl group preferably having from 1 to 5 carbon atoms and more preferably from 1 to 3 carbon atoms, such as a methyl group, an ethyl group, a propyl group, and a butyl group; an alkoxycarbonyl group preferably having from 2 to 6 carbon atoms and more preferably from 2 to 4 carbon atoms, such as a methoxycarbonyl group, an ethoxycarbonyl group, a propoxycarbonyl group, and a butoxycarbonyl group; or a dialkylamino group preferably having the alkyl moiety of from 1 to 5 carbon atoms and more preferably from 1 to 3 carbon atoms (e.g., methyl, ethyl, propyl, and butyl), such as a dimethyl amino group. Of these, a halogen atom, an alkyl group, an alkoxycarbonyl group, and a dialkylamino group are preferred.

Specific examples of the TCNAQ derivatives represented by formula (I) according to the present invention are shown below (wherein Me and Bu represents a methyl group and a butyl group, respectively):

-continued

-continued

Specific examples of the anthraquinone derivatives represented by formula (III) which can be used as starting material for preparing the TCNAQ derivatives of the present invention are shown below:

The tertiary organic base to be used as a catalyst in combination with titanium tetrachloride includes pyridine and quinoline, with pyridine being preferred.

The condensation reaction between the compound of formula (II) and the anthraquinone derivative of formula (III) can be carried out as follows. The anthraquinone derivative of formula (III) is dissolved or suspended in a solvent, such as chloroform, dioxane, tetrahydrofuran (THF), methylene chloride, benzene, nitromethane, etc., to which titanium tetrachloride is added, optionally with cooling. To the resulting suspension is added a solution containing malononitrile and a tertiary organic base, and the suspension is then heated at reflux for 1 to 10 hours, preferably 2 to 3 hours while confirming the progress of the reaction by thin layer chromatography. After completion of the reaction, the reaction solution is poured into ice-water, and the precipitated inorganic salts are removed by filtration. The filtrate is extracted with a solvent and, if desired, the extract is concentrated. The extract or the concentrate thereof is treated with an appropriate medium to precipitate a crude product, which is then purified by recrystallization or the like means to obtain a purified product.

In the reaction, malononitrile is generally added in an amount of 4 moles or more, preferably from 6 to 20 moles, and more preferably from 6 to 10 moles per mole of the anthraquinone derivative. Further the amount of titanium tetrachloride added is generally 2 moles or more, more preferably from 3 to 10 moles and most preferably from 3 to 5 moles, and the amount of the tertiary organic base is generally added in an amount of from 10 to 40 moles.

The TCNAQ derivatives according to the present invention can be used as charge transport materials for electrophotographic photoreceptors. In this application, the TCNAQ derivative may be dispersed in a resin binder, e.g., polycarbonate, polyester, etc., to form a charge transport layer, or mixed with a charge generating material to form a charge generating layer. The amounts of the TCNAQ derivative in the former case and the latter case are generally from 10 to 70 wt % and less than 50 wt %, respectively, based on the total amount of the resulting layer.

While the TCNAQ derivatives of formula (I) per se sufficiently function as charge transport materials, those wherein the two substituents represented by R are selected from a halogen atom, a cyano group, a nitro group, an alkyl group, and an alkoxycarbonyl group (particularly preferably from a cyano group, a halogen atom, a methyl group and a methoxycarbonyl group) can also be used in the form of a charge transfer complex with an electron donor, and those having the substituents bonded to positions selected from 2-, 3-, 6-, and 7-positions are preferred as starting material for forming a charge transfer complex.

The electron donor which can be used for the formation of a charge transfer complex includes aromatic compounds such as benzene, naphthalene, anthracene, phenanthrene, pyrene, and perylene-; p-phenylenediamine and analogous condensed ring aromatic amines; sulfur-containing electron donating compounds such as tetrathiafulvalene (TTF), tetrathiatetracene (TTT), and tetramethyltetrathiafulvalene (TMTSF); hydrazones such as p-diethylaminobenzaldehydo-N,N-diphenylhydrazone, p-diethylaminobenzaldehydo-N,N-di(p-methoxyphenyl)-hydrazone, p-diethylaminobenzaldehydo-N-(α-naphthyl)-N-phenylhydrazone, and β,β-di(4-methoxyphenyl)acroleindiphenylhydrazone; triarylmethane compounds such as bis(4-diethylamino-2-methlphenyl)-phenylmethane; triarylamine compounds such as triphenylamine, 2,4′,4″-trimethyltriphenylamine, and 1,1-bis{4′-N,N-di(p-methylphenyl)aminophenyl}cyclohexane; and benzidine compounds such as N,N′-diphenyl-N,N′-bis(3-methylphenyl)-{1,1′-biphenyl}-4,4′-diamine, and 3,3′-dimethyl-N,N,N′N′-tetrakis(4-methylphenyl)-{1,1′-biphenyl}-4,4′-diamine. Of these, those having an ionization potential of 7 eV or less (more preferably from 5 to 6 eV) are preferred, and π-type electron donating compounds are more preferred. Such π-type electron donating compounds include benzene, naphthalene, anthracene, phenanthrene, pyrene, perylene, TTF, TTT, etc.

The charge transfer complex according to the present invention can be prepared as a solid product by dissolving the TCNAQ derivative of formula (I) (excluding those having a dialkylamine group for R) and an excess of an electron donating compound in a combination of solvents to cause reaction to form a charge transfer complex and then precipitating the formed complex. If desired, the reaction solution may be heated.

In one embodiment of the above-described process, the starting materials are dissolved in a mixed solvent consisting essentially of (1) a solvent capable of dissolving both starting materials and favorable for formation of a charge transfer complex (e.g., methylene chloride, chloroform, benzene, dichloroethane, etc.) and (2) a solvent capable of dissolving the electron donating compound used in excess but poor for the formed charge transfer complex (e.g., ether, carbon tetrachloride, etc.). After completion of the reaction, the solvent (1) is evaporated by heating the solution to thereby precipitate the charge transfer complex, which is collected by filtration and washed with a poor solvent to remove any electron donating compound remaining in the complex. This embodiment can be adopted in the cases where the solvent (1) has a lower boiling point than that of the solvent (2) or in the cases where the electron donating compound used is relatively sparingly soluble in the solvent (1). In these cases, the solvent (1) is used in an amount enough to dissolve both of the starting materials.

In another embodiment of the above-described process, the starting materials are dissolved in the solvent (1) (e.g., methylene chloride, chloroform, benzene, acetone, dichloroethane, etc.) to cause the reaction, and the solvent (2) (e.g., ether, carbon tetrachloride, ethanol, hexane, petroleum ether, etc.) is then added to the reaction solution to thereby precipitate the formed charge transfer complex, which is then collected by filtration. This embodiment is adopted in the cases where the boiling point of the solvent (1) is higher than that of the solvent (2). In this embodiment, the solvent (2) should be added in an amount enough to precipitate the reaction product.

In either embodiment, each of the two starting materials may be separately dissolved in the mixed solvent or the solvent (1) and the solutions are then combined, or both of them may be simultaneously dissolved in the mixed solvent. When it is difficult to dissolve, the system may be heated at a temperature not higher than a reflux temperature.

While examples of the solvent (1) includes chlorinated hydrocarbons, e.g., methylene chloride, dichloroethane, etc., acetone and the like and examples of the poor solvent (2) include alcohols, carbon tetrachloride and the like, as described above, dichloroethane may serve as a poor solvent in some cases. Preferred combinations of the solvents (1) and (2) are methylene chloride/carbon tetrachloride, and methylene chloride/alcohol.

The charge transfer complex of the present invention can also be prepared by simultaneously sublimating the TCNAQ derivative and a subliming electron donating compound, e.g., phenanthrene, pyrene, etc., under high vacuum to directly obtain a complex.

The thus prepared charge transfer complexes according to the present invention are crystalline solids colored in purple, yellow, orange, green or the like color which have a melting point ranging from 100° to 300° C. and show spectra inherent to complexes. They have high electrical conductivities. In NMR analysis of the charge transfer complexes, they are dissociated in a solution to create an equilibrium state so that they also exhibit absorption spectrum of each of the electron donating compound and the TCNAQ derivative.

The present invention will now be illustrated in greater detail with reference to the following examples, but it should be understood that these examples are not deemed to limit the present invention.

EXAMPLE 1

Preparation of 2,6-Dichloro TCNAQ

In 80 ml of dry chloroform was suspended 2.23 g of 2,6-dichloroanthraquinone, and 3.6 ml (4 molar equivalents (=moles/mole of the anthraquinone; hereafter referred to as "eq.") of titanium tetrachloride was added to the suspension. A solution of 10.6 g (20 eq.) of malononitrile and 26 ml (40 eq.) of dry pyridine in 80 ml of dry chloroform was added thereto dropwise over 25 minutes, followed by refluxing for 3 hours. The reaction mixture was poured into 200 ml of water, and the precipitated inorganic salts were separated by filtration. After liquid separation, the aqueous layers were combined and extracted three times with 200 ml portions of methylene chloride The combined organic layer was washed four times with 200 ml portions of water and dried over sodium sulfate. The solvent was removed by distillation under reduced pressure to obtain 5.44 g of a purple tar-like substance. To the product was added 50 ml of diethyl ether to crystallize. The crude product collected by filtration weighing 2.13 g was purified by column chromatography using 50 g of silica gel to obtain 2.03 g of 2,6-dichloro TCNAQ as a methylene chloride eluate (yield: 68%). Recrystallization from a mixture of acetonitrile and carbon tetrachloride gave crystals having a melting point of 292° to 294° C.

Elementary Analysis for $C_{20}H_6N_4Cl_2$: Calcd. (%): C 64.37; H 1.62; N 15.01; Cl 18.99; Found (%): C 64.96; H 1.30; N 15.04; Cl 19.07.

$^1$H-NMR (60 MHz;

$\delta^{CDCl_3}_{ppm}$:

8.26 (2H, d, J=2 Hz), 8.20 (2H, d, 9 Hz), 7.73 (2H, dd, J=2 Hz, 9 Hz).

IR (KBr; $\bar{\nu}$ cm$^{-1}$): 3100, 3080, 2230, 1595, 1560, 1315, 840.

EXAMPLE 2

Preparation of 2,6-Dibromo TCNAQ

In 27 ml of dry chloroform was suspended 1.0 g of 2,6-dibromoanthraquinone, and 3.5 ml (4 eq.) of titanium tetrachloride was added to the suspension. A solution of 3.60 g (20 eq.) of malononitrile and 9 ml (40 eq.) of dry pyridine in dry chloroform was added thereto dropwise over 30 minutes, followed by refluxing for 3 hours. The reaction mixture was poured into 150 ml of water, and the precipitated inorganic salts were separated by filtration. The aqueous layer was extracted three times with 100 ml portions of methylene chloride. The combined organic layer was washed four times with 100 ml portions of water and dried over sodium sulfate. The solvent was removed by distillation under reduced pressure to obtain 1.43 g of a brown tar-like substance. The product was subjected to column chromatography using 35 g of silica gel and eluted with methylene chloride. The resulting solid weighing 850 mg was washed with 10 ml of methanol to obtain 830 g of 2,6-dibromo TCNAQ in a yield of 66%. Recrystallization from a mixture of methylene chloride and ethanol gave a purified product having a melting point of 291°–293° C.

Elementary Analysis for $C_{20}H_6Br_2N_4$: Calcd. (%): C 51.98; H 1.31; N 12.12; Br 34.58; Found (%): C 52.29; H 1.12; N 12.10; Br 34.30.

$^1$H-NMR (60 MHz, $\delta_{ppm}^{CDCl_3}$):

8.47 (2H, d, 3 Hz), 8.21 (2H, d, J=9 Hz), 7.98 (2H, dd. J=3 Hz, 9 Hz)

IR (KBr, $\bar{\nu}$ cm$^{-1}$): 3100, 3060, 3020, 2210, 1590, 1550, 1540, 1310, 830.

EXAMPLE 3

Preparation of 2,6-Bis(methoxycarbonyl) TCNAQ

In 18 ml of dry chloroform was dissolved 600 mg of dimethyl anthraquinone-2,6-dicarboxylate, and 0.8 ml (4 eq.) of titanium tetrachloride was added to the solution. A solution of 1.22 g (10 eq.) of malononitrile and 6 ml (40 eq.) of dry pyridine in 18 ml of dry chloroform was added thereto dropwise over 20 minutes, followed by refluxing for 4 hours. The reaction mixture was poured into 200 ml of water. After separating inorganic salts by filtration, the aqueous layer was extracted three times with 100 ml portions of methylene chloride. The combined organic layer was washed four times with 100 ml portions of water and dried over sodium sulfate. The solvent was removed by distillation under reduced pressure to obtain 590 mg of a green tar, which was then subjected to column chromatography using 20 g of silica gel and eluted with methylene chloride to separate 511 mg of a crude product. Recrystallization of the crude product from a mixture of diethyl ether and hexane gave 329 mg of 2,6-bis(methoxycarbonyl) TCNAQ having a melting point of 110° to 120° C. (decomp.) in a yield of 42%.

Elementary Analysis for $C_{24}H_{12}N_4O_4$: Calcd. (%): C 68.57; H 2.88; N 13.33; Found (%): C 68.38; H 3.12; N 12.79.

$^1$H-NMR (60 MHz; $\delta_{ppm}^{CDCl_3}$):

9.04 (2H, s), 8.50 (4H, s), 4.06 (6H, s).

IR (KBr, $\bar{\nu}$ cm$^{-1}$): 3080, 3000, 2950, 2850, 2220, 1730, 1610, 1570, 1440, 1290, 1250, 765, 690.

EXAMPLE 4

Preparation of 2,6-Dimethyl TCNAQ

In 60 ml of dry chloroform was dissolved 1.50 g of 2,6-dimethylanthraquinone, and 2.8 ml (4 eq.) of titanium tetrachloride was added to the solution. A solution of 8.40 g (20 eq.) of malononitrile and 20 ml (40 eq.) of dry pyridine in 60 ml of dry chloroform was added thereto dropwise over 30 minutes, followed by refluxing for 3.5 hours. The reaction mixture was poured into 250 ml of water, and inorganic salts were removed by filtration. After liquid separation, the aqueous layer was extracted three times with 100 ml portions of methylene chloride, and the organic layer were combined, washed four times with 150 ml portions of water, and dried over sodium sulfate. The solvent was removed by distillation under reduced pressure to obtain 5.0 g of red tar, which was then subjected to column chromatography using 50 g of silica gel and eluted with a mixture of methylene chloride and hexane (4:1 by volume) to obtain 2.35 g of a yellow waxy solid. The solid was washed with 50 ml of diethyl ether to obtain 1.83 g of 2,6-dimethyl TCNAQ (yield: 87%). Recrystallization from a mixture of methylene chloride and hexane yielded a purified product having a melting point of 270° to 272° C.

Elementary Analysis for $C_{22}H_{14}N_4$: Calcd. (%): C 79.50; H 3.64; N 16.86; Found (%): C 79.96; H 3.43; N 16.87.

$^1$H-NMR (60 MHz, $\delta_{ppm}^{CDCl_3}$):

8.20 (2H, d, J=8 Hz), 8.10 (2H, s), 7.56 (2H, d, J=8 Hz), 2.53 (6H, s).

IR (KBr, $\bar{\nu}$ cm$^{-1}$): 2220, 1610, 1550, 1320, 1270, 820.

EXAMPLE 5

Preparation of 1,5-Dichloro TCNAQ

In 160 ml of dry chloroform was suspended 4.43 g of 1,5-dichloroanthraquinone, and 7 ml (4 eq.) of titanium tetrachloride was added to the suspension. To the mixture was added dropwise a solution of 21.2 g (20 eq.) of malononitrile and 50 ml (40 eq.) of dry pyridine in 160 ml of dry chloroform. After refluxing for 115 hours, the reaction mixture was poured into 300 ml of water, followed by filtration to remove inorganic salts. After liquid separation, the aqueous layer was extracted three times with 100 ml portions of methylene chloride, and the combined organic layer was washed five times with 200 ml portions of water and dried over sodium sulfate. The solvent was removed by distillation under reduced pressure to obtain 8.78 g of a solid, which was washed with diethyl ether to obtain 3.80 g of a crude product. The crude product was recrystallized from a mixture of acetone and acetonitrile to obtain 3.21 g (54%) of 1,5-dichloro TCNAQ having a melting point of 365° to 370° C. (decomp.).

IR (KBr, $\bar{\nu}$ cm$^{-1}$): 3100, 2230, 1590, 1585, 1580, 1515, 1320, 790.

EXAMPLE 6

Preparation of 2,7-Bis(methoxycarbonyl) TCNAQ

In 50 ml of dry chloroform was dissolved 1.70 g of dimethyl anthraquinone-2,7-dicarboxylate, and 2.3 ml (4 eq.) of titanium tetrachloride was added to the solution. A solution of 3.46 g (10 eq.) of malononitrile and 17 ml (40 eq.) of dry pyridine in dry chloroform was added dropwise to the mixture over one hour, followed by refluxing for one hour. The reaction mixture was poured into 200 ml of water, and inorganic salts were removed by filtration. After liquid separation, the aqueous layer was extracted three times with 50 ml portions of methylene chloride. The combined organic layer was washed three times with 150 ml of water and dried over sodium sulfate. The solvent was removed by distillation under reduced pressure to obtain 5 g of a red tar, which was then subjected to column chromatography using 50 g of silica gel and eluted with methylene chloride to obtain 1.76 g of a green tar. The resulting product was dissolved in 150 ml of benzene and washed three times with 100 ml portions of 2N hydrochloric acid. The organic layer was washed twice with 50 ml portions of water and then with 50 ml of a saturated aqueous solution of sodium chloride, and dried over sodium sulfate. To the residue was added 30 ml of hexane, and the solvent was distilled off to isolate 954 mg (yield: 36%) of 2,7-bis(methoxycarbonyl) TCNAQ-benzene complex having a melting point of 130°+145° C. (decomp.).

The single compound may also be obtained by dissolving the resulting benzene complex in methylene chloride, removing the solvent by distillation under reduced pressure, and recrystallizing the resulting tar-like substance from a mixture of methylene chloride and hexane. The resulting product had a melting point of 125°-150° C. (decomp.).

$^1$H-NMR (60 MHz, $\delta^{CDCl_3}_{ppm}$):

8.95 (2H, s), 8.40 (4H, s), 4.00 (6H, s).

IR (KBr, $\bar{\nu}$ cm$^{-1}$): 2970, 2240, 1735, 1610, 1570, 1560, 1440, 1290, 1260, 1200, 1185, 1120, 1100, 760, 690.

EXAMPLE 7

Preparation of 2,7-Dimethyl TCNAQ

In 50 ml of dry chloroform was dissolved 1.29 g of 2,7-dimethylanthraquinone, and 2.4 ml (4 eq.) of titanium tetrachloride was added thereto. To the mixture was added dropwise a solution of 7.20 g (20 eq.) of malononitrile and 17 ml (40 eq.) of dry pyridine in dry chloroform over 30 minutes. After refluxing for 3 hours, the reaction mixture was poured into 300 ml of water. The mixture was filtered to separate inorganic salts, followed by liquid separation. The aqueous layer was extracted three times with 50 ml portions of methylene chloride, and the organic layers were combined, washed three times with 150 ml portions of water, and dried over sodium sulfate. The solvent was removed by distillation under reduced pressure to obtain 2.84 g of a brown tar. The product was subjected to column chromatography using 50 g of silica gel and eluted with methylene chloride to obtain a yellow tar. To the tar was added 10 ml of diethyl ether to crystallize, followed by filtration. The resulting crude product weighing 1.43 g was recrystallized from a mixture of methylene chloride and hexane to obtain 1.13 g (yield: 63%) of 2,7-dimethyl TCNAQ having a melting point of 268°-269° C.

Elementary Analysis for C$_{22}$H$_{14}$N$_4$: Calcd. (%): C 79.50; H 3.64; N 16.86; Found (%): C 79.77; H 3.38; N 16.97.

$^1$H-NMR (60 MHz, $\delta^{CDCl_3}_{ppm}$):

2.53 (6H, s), 7.58 (2H, d, J=12 Hz), 8.12 (2H, s), 8.25 (2H, d, J=12 HZ).

IR (KBr, $\bar{\nu}$ cm$^{-1}$): 2230, 1610, 1600, 1585, 1555, 1540, 1480, 1330, 1310, 1270, 830, 820, 695, 580, 460.

EXAMPLE 8

Preparation of 2,3-Dimethyl TCNAQ

In 85 ml of dry chloroform was dissolved 2.0 g of 2,3-dimethylanthraquinone, and 3.7 ml (4 eq.) of titanium tetrachloride was added to the solution. To the mixture was added dropwise a solution of 11.2 g (20 eq.) of malononitrile and 27 ml (40 eq.) of dry pyridine in 80 ml of dry chloroform over 25 minutes. After refluxing for 4.5 hours, the reaction mixture was poured into 200 ml of water, followed by filtration to remove inorganic salts. After liquid separation, the aqueous layer was extracted three times with 100 ml portions of methylene chloride, and the organic layers were combined, washed six times with 200 ml portions of water, and dried over sodium sulfate. The solvent was removed by distillation under reduced pressure to obtain a brown tar, which was then crystallized from 30 ml of acetonitrile. The crude product weighing 2.33 g was recrystallized from acetonitrile to obtain 2.11 g (yield: 75%) of 2,3-dimethyl TCNAQ having a melting point of 301°-302° C.

$^1$H-NMR (60 MHz, $\delta^{CDCl_3}_{ppm}$):

2.43 (6H, s), 7.7-7.9 (2H, m), 8.10 (2H, s), 8.2-8.4 (2H, m).

IR (KBr, $\bar{\nu}$ cm$^{-1}$): 2210, 1605, 1580, 1550, 1535, 1325, 1270, 765, 685, 460.

EXAMPLE 9

Preparation of 2-Dimethylamino TCNAQ

In 200 ml of dry chloroform was suspended 6.19 g of 2-dimethylaminoanthraquinone, and 19.8 g of titanium tetrachloride was added thereto, followed by stirring. To the mixture was added dropwise a solution of 34.4 g of malononitrile and 82.7 g of dry pyridine in 200 ml of dry chloroform over about 10 minutes, and the mixture was heat-refluxed for 5.5 hours. After the reaction, the reaction mixture was poured into 1.2 l of ice-water, followed by filtration to separate inorganic salts. The filtrate was subjected to liquid separation, and the aqueous layer was extracted twice with chloroform. The combined organic layer was washed with water and dried over sodium sulfate. The solvent was removed by distillation, and methanol was added to the residue, followed by filtration to obtain 7.91 g of reddish purple crystals in a yield of 92%. Recrystallization from chloroform gave a product having a melting point of from 317° C. (decomp.)

Elementary Analysis for C$_{22}$H$_{13}$N$_5$: Calcd. (%): C 76.07; H 3.77; N 20.16; Found (%): C 75.96; H 3.76; N 20.05.

Figure 1:
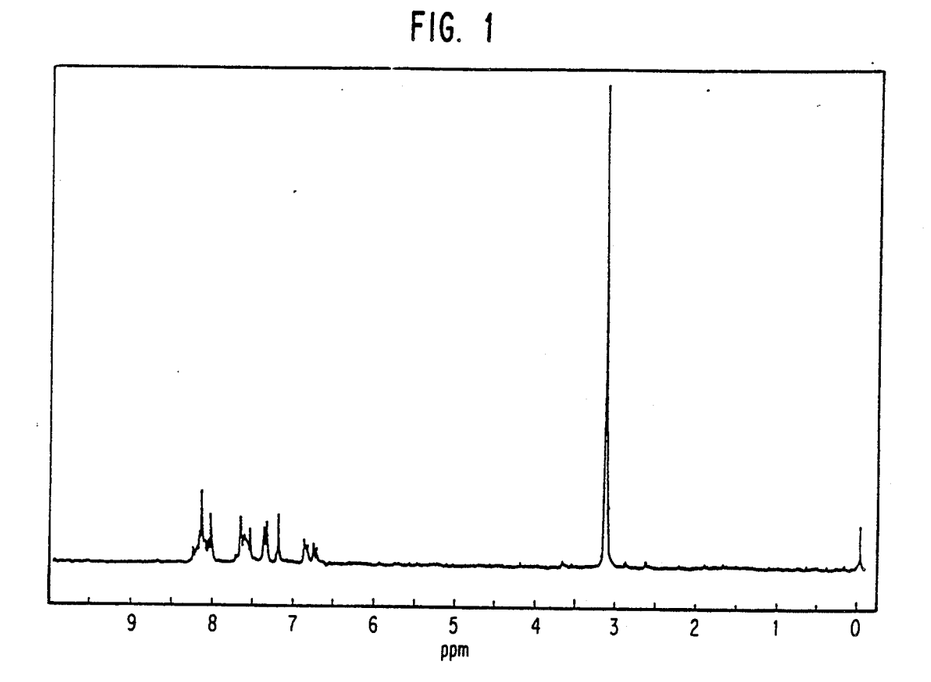
FIGS. 1 and 3 each shows an NMR spectrum of the TCNAQ derivative according to the present invention.
Figure 2:
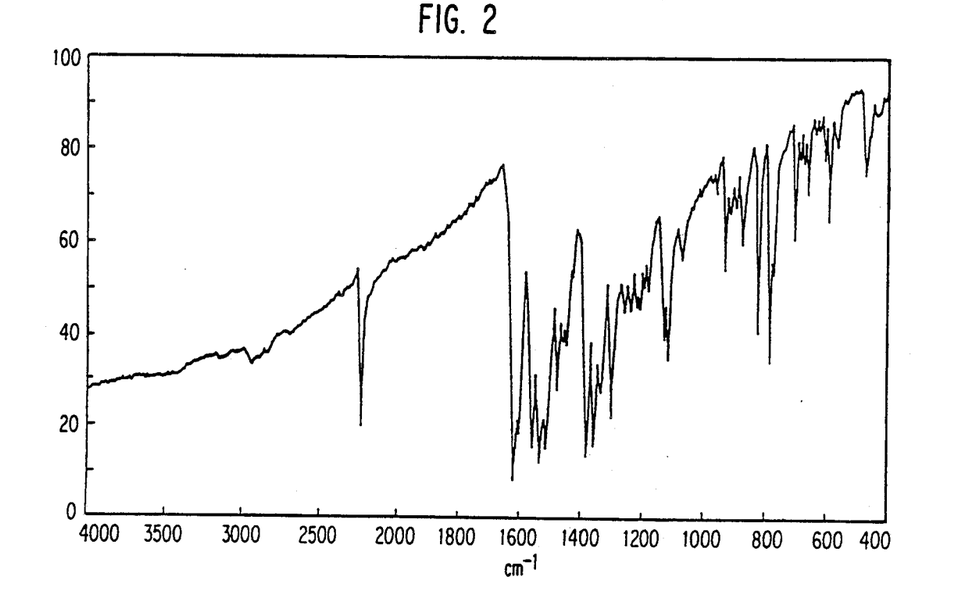
FIG. 2 and 4 each shows an IR spectrum of the TCNAQ derivative according to the present invention.

$^1$H-NMR Spectrum shown in FIG. 1.
IR Spectrum (KBr): shown in FIG. 2.

EXAMPLE 10

Preparation of 2,6-Bis(dimethylamino) TCNAQ

One gram of 2,6-bis(dimethylamino)anthraquinone was suspended in 35 ml of dry chloroform, and 1.5 ml (4 eq.) of titanium tetrachloride was added to the suspension. A solution of 4.5 g (20 eq.) of malononitrile and 11 ml (40 eq.) of dry pyridine in dry chloroform was added dropwise thereto over 30 minutes. The mixture was refluxed for 9 hours and then poured into 150 ml of water, followed by filtration to separate inorganic salts. After liquid separation, the aqueous layer was extracted twice with 100 ml portions of methylene chloride. The organic layers were combined, washed three times with 150 ml portions of water, and dried over sodium sulfate. The solvent was removed by distillation to obtain a black solid, which was subjected to obtain 776 mg of 2,6-bis(dimethylamino) TCNAQ as a sparingly soluble fraction in a yield of 58%. Recrystallization from a mixture of methylene chloride and carbon tetrachloride gave a product having a melting point of 337°–338° C. (decomp.).

Elementary Analysis for $C_{24}H_{18}N_6$: Calcd. (%): C 73.83; H 4.65; N 21.53; Found (%): C 73.78; H 4.55; N 21.53.

Figure 3:
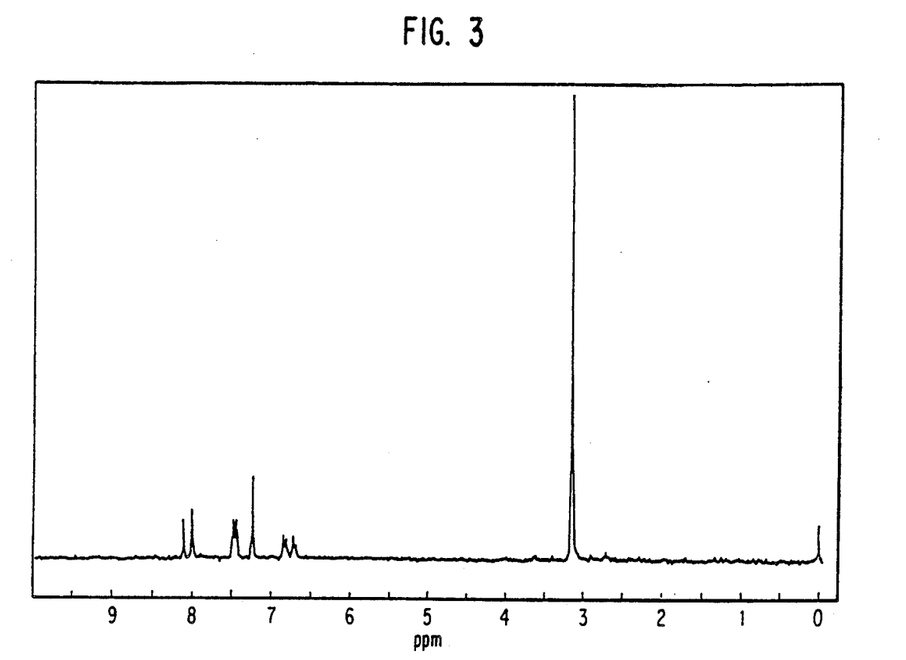
Figure 4:
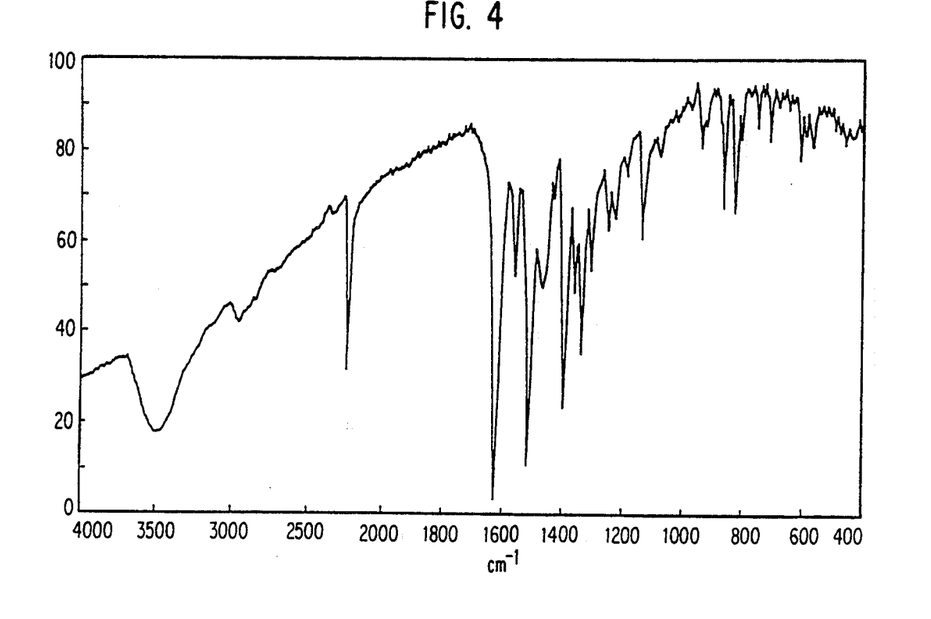

$^1$H-NMR Spectrum: shown in FIG. 3.
IR Spectrum (KBr): shown in FIG. 4.

EXAMPLE 11

Preparation of 2,6-Dichloro TCNAQ-Naphthalene (1:1) Complex

In 2 ml of methylene chloride were dissolved 50 mg of 2,6-dichloro TCNAQ and 100 mg (large excess) of naphthalene under heating at a reflux temperature of about 40° C., and the resulting solution was concentrated to 0.5 ml. The precipitated crystals were collected by filtration and washed with a small amount of cold 1,2-dichloroethane to obtain 35 mg of the entitled complex having a melting point of 123°–200° C. (decomp.)

Figure 5:
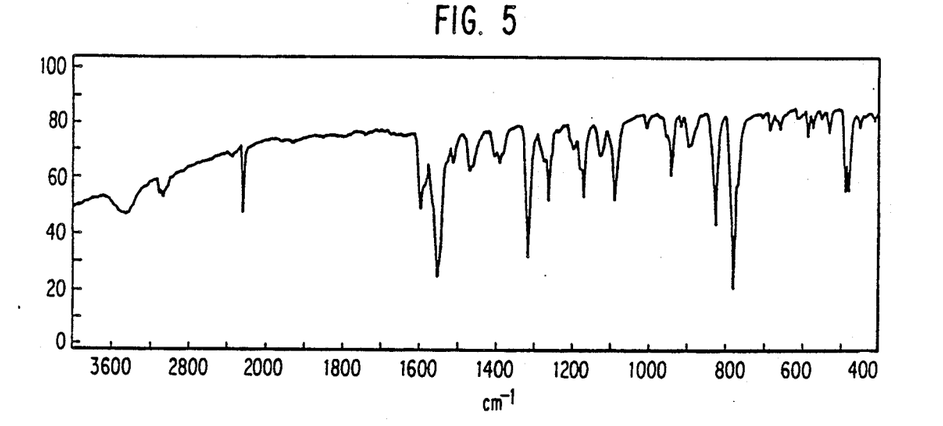
FIGS. 5 to 10 each shows an IR absorption spectrum of the TCNAQ-based charge transfer complex according to the present invention.

IR Spectrum (KBr): shown in FIG. 5.

Elementary Analysis for $C_{30}H_{14}N_4Cl_2$: Calcd. (%): C 71.89; H 2.81; N 11.17; Cl 14.14; Found (%): C 71.93; H 2.54; N 11.19; Cl 14.04.

EXAMPLE 12

Preparation of 2,6-Dichloro TCNAQ-Phenanthrene (1:1) Complex

In 2 ml of hot methylene chloride (about 40° C.) was dissolved 50 ml of 2,6-dichloro TCNAQ, and 48 mg (2 eq.) of phenanthrene was added to the solution. To the solution was added 1 ml of ethanol, and the mixture was concentrated to 2 ml, followed by allowing to cool. The concentrate was filtered, and the filter cake was washed with ethanol to obtain 72 mg of vermilion flaky crystals having a melting point of 166°–250° C. (decomp.).

Figure 6:
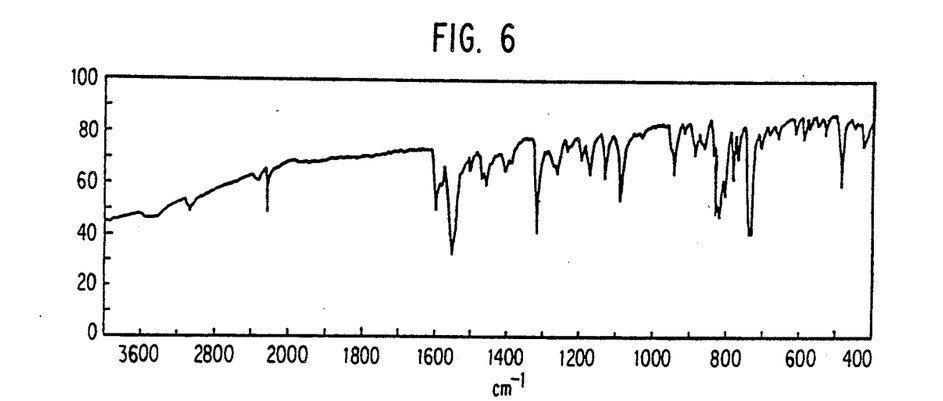

IR Spectrum (KBr): shown in FIG. 6.

Elementary Analysis for $C_{34}H_{16}N_4Cl_2$: Calcd. (%): C 74.06; H 2.92; N 10.16; Cl 12.86; Found (%): C 73.98; H 2.70; N 10.00; Cl 13.28.

EXAMPLE 13

Preparation of 2,6-Dichloro TCNAQ-Pyrene (1:1) Complex

In 2 ml of hot methylene chloride were dissolved 50 mg of 2,6-dichloro TCNAQ and 54 mg (2 eq.) of pyrene, and 1 ml of ethanol was added to the solution. The solution was allowed to cool and filtered. The filter cake was washed with ethanol to obtain 64 mg of the entitled complex as a purple flaky crystal having a melting point of 204°–206° C.

Elementary Analysis for $C_{36}H_{16}N_4Cl_2$: Calcd. (%): C 75.13; H 2.80; N 9.74; Cl 12.32; Found (%): C 75.40; H 2.51; N 9.71; Cl 12.30.

EXAMPLE 14

Preparation of 2,6-Dichloro TCNAQ-2,3,5,6-Tetramethyl-p-phenylenediamine (1:1) Complex In 2 ml of hot methylene chloride was dissolved 50 mg of 2,6-dichloro TCNAQ, and 44 mg (2 eq.) of 2,3,5,6-tetramethyl-p-phenylenediamide was added to the solution. Immediately after the addition, a green precipitate began to appear. After allowing to cool, the solution was filtered, and the filter cake was washed with carbon tetrachloride to obtain 53 mg of the entitled complex as a green crystal having a melting point of 208°–210° C. (decomp.).

Elementary Analysis for $C_{30}H_{22}N_6Cl_2$: Calcd. (%): C 67.04; H 4.13; N 15.64; Cl 13.19; Found (%): C 67.28; H 4.01; N 15.57; Cl 13.34.

EXAMPLE 15

Preparation of 2,6-Dichloro TCNAQ-TTF (2:1) Complex

In 2 ml of hot methylene chloride was dissolved 50 mg of 2,6-dichloro TCNAQ, and 55 mg (2 eq.) of TTF was added thereto. The solution was concentrated to 1 ml, followed by allowing to cool. After filtration, the solid was washed with carbon tetrachloride to obtain 40 mg of the entitled complex as a dark blue crystal having a melting point of 219°–223° C. (decomp.).

Elementary Analysis for $C_{23}H_8N_4Cl_2S_2$: Calcd. (%): C 58.11; H 1.70; N 11.79; Cl 14.92; S 13.49; Found (%): C 57.81; H 1.57; N 11.56; Cl 15.14; S 13.39.

EXAMPLE 16

Preparation of 2,6-Dibromo TCNAQ-Naphtalene (2:1) Complex

In 2 ml of hot methylene chloride was dissolved 50 mg of 2,6-dibromo TCNAQ, and 100 mg (large excess) of naphthalene was added thereto. The solution was concentrated to 0.5 ml, followed by allowing to cool. After filtration, the solid was washed with a small amount of cold 1,2-dichloroethane to obtain 14 mg of the entitled complex as a vermilion powder having a melting point of 110°–120° C. (decomp.).

Elementary Analysis for $C_{25}H_{10}N_4Br_2$: Calcd. (%): C 57.06; H 1.92; N 10.65; Br 30.37; Found (%): C 57.55; H 1.73; N 10.50; Br 30.03.

EXAMPLE 17

Preparation of 2,6-Dibromo TCNAQ-Phenanthrene (1:1) Complex

In 2 ml of hot methylene chloride was dissolved 50 mg of 2,6-dibromo TCNAQ, and 39 mg (2 eq.) of phenanthrene was added thereto. To the solution was added 1 ml of ethanol, and the solution was concentrated to 2 ml. After allowing to cool, the solution was filtered, and the filter cake was washed with ethanol to obtain 58 mg of the entitled complex as a vermilion flaky crystal having a melting point of 197°–250° C. (decomp.).

Elementary Analysis for $C_{34}H_{16}N_4Br_2$: Calcd. (%): C 63.77; H 2.52; N 8.75; Br 24.96; Found (%): C 63.17; H 2.36; N 8.61; Br 25.66.

EXAMPLE 18

Preparation of 2,6-Dibromo TCNAQ-Pyrene (1:1) Complex

In 2 ml of hot methylene chloride was dissolved 50 mg of 2,6-dibromo TCNAQ, and 44 mg (2 eq.) of pyrene was added thereto. To the solution was added 1 ml of ethanol, and the mixture was concentrated to 1.5 ml, followed by allowing to cool. The concentrate was filtered, and the filter cake was washed with ethanol to obtain 70 mg of the entitled complex as a purple crystal having a melting point of 220°–221° C.

Elementary Analysis for $C_{36}H_{16}N_4Br_2$: Calcd. (%): C 65.08; H 2.43; N 8.43; Br 24.06; Found (%): C 65.07; H 2.17; N 8.41; Br 24.14.

EXAMPLE 19

Preparation of 2,6-Dibromo TCNAQ-2,3,5,6-Tetramethyl-p-phenylenediamine (1:1) Complex In 3 ml of hot methylene chloride was dissolved 50 mg of 2,6-dibromo TCNAQ, and 35 mg (2 eq.) of 2,3,5,6-tetramethyl-p-phenylenediamine was added thereto. The solution was concentrated to 2 ml. The concentrate was allowed to cool and filtered. The filter cake was washed with carbon tetrachloride to obtain 30 mg of the entitled complex as a green powder having a melting point of 212°–213° C. (decomp.).

Elementary Analysis for $C_{30}H_{22}N_6Br_2$: Calcd. (%): C 57.53; H 3.54; N 13.42; Br 25.52; Found (%): C 57.45; H 3.40; N 13.39; Br 25.82.

EXAMPLE 20

Preparation of 2,6-Dibromo TCNAQ-TTF (1:1) Complex

In 2 ml of hot methylene chloride was dissolved 50 mg of 2,6-dibromo TCNAQ, and 44 mg (2 eq.) of TTF was added thereto. The solution was concentrated to 1 ml, and the concentrate was allowed to cool, followed by filtration. The filter cake was washed with carbon tetrachloride to obtain 54 mg of the entitled complex as a deep blue crystal having a melting point of 175°–180° C. (decomp.).

Elementary Analysis for $C_{26}H_{10}N_4Br_2S_4$: Calcd. (%): C 46.85; H 1.51; N 8.41; Br 23.98; S 19.24; Found (%): C 46.62; H 1.37; N 8.41; Br 24.72; S 18.16.

EXAMPLE 21

Preparation of 2,6-Bis(methoxycarbonyl) TCNAQ-Anthracene (2:1) Complex

In a mixed solvent comprising 1 ml of methylene chloride and 2 ml of diethyl ether were dissolved 40 mg of 2,6-bis(methoxycarbonyl) TCNAQ and 8 mg (0.5 eq.) of anthracene under heating, and the solution was concentrated to obtain a purple tar-like substance. The product was suspended in 3 ml of diethyl ether, followed by filtration. The filter cake was washed with diethyl ether to obtain 15 mg of the entitled complex as a purple powder having a melting point of 194°–195° C.

Elementary Analysis for $C_{31}H_{17}N_4O_4$: Calcd. (%): C 73.08; H 3.36; N 11.00; Found (%): C 73.07; H 3.12; N 10.99.

EXAMPLE 22

Preparation of 2,6-Bis(methoxycarbonyl) TCNAQ-Phenanthrene (2:1) Complex

In 2 ml of hot methylene chloride were dissolved 40 mg of 2,6-bis(methoxycarbonyl) TCNAQ and 8 mg (0.5 eq.) of phenanthrene, and the solution was concentrated to obtain a vermilion tar-like substance. The product was suspended in 2 ml of diethyl ether, followed by filtration. The solid was washed with diethyl ether to obtain 13 mg of the entitled complex as a vermilion powder having a melting point of 225°–228° C.

Elementary Analysis for $C_{31}H_{17}N_4O_4$: Calcd. (%): C 73.08; H 3.36; N 11.00; Found (%): C 72.41; H 3.09; N 10.99.

EXAMPLE 23

Preparation of 2,6-Bis(methoxycarbonyl) TCNAQ-Pyrene (2:1) Complex

In 2 ml of hot methylene chloride were dissolved 40 mg of 2,6-bis(methoxycarbonyl) TCNAQ and 10 mg (0.5 eq.) of pyrene, and the solution was concentrated to obtain a purple tar-like substance. The product was suspended in 3 ml of diethyl ether, followed by filtration. The solid was washed with diethyl ether to obtain 29 mg of the entitled complex as a purple powder having a melting point of 258°–260° C.

Figure 7:
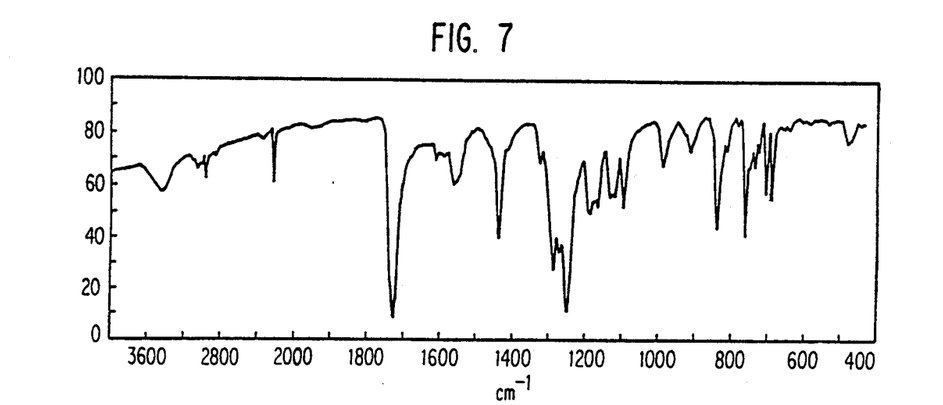

IR Spectrum (KBr): shown in FIG. 7.

Elementary Analysis for $C_{32}H_{17}N_4O_4$: Calcd. (%): C 73.70; H 3.29; N 10.74; Found (%): C 73.28; H 3.10; N 10.78.

EXAMPLE 24

Preparation of 2,6-Bis(methoxycarbonyl) TCNAQ-2,3,5,6-Tetramethyl-p-phenylenediamine (2:1) Complex In 2 ml of hot methylene chloride were dissolved 40 mg of 2,6-bis(methoxycarbonyl) TCNAQ and 8 mg (0.5 eq.) of 2,3,5,6-tetramethyl-p-phenylenediamine, and the solution was concentrated to obtain a green to black tar-like substance. The product was suspended in 3 ml of diethyl ether, followed by filtration. The filter cake was washed with diethyl ether to obtain 23 mg of the entitled complex as a greenish black powder having a melting point of 205°–206° C. (decomp.).

Elementary Analysis for $C_{29}H_{20}N_5O_4$: Calcd. (%): C 69.32; H 4.01; N 13.94; Found (%): C 69.25; H 3.97; N 13.74.

EXAMPLE 25

2,6-Bis(methoxycarbonyl) TCNAQ-TTF (2:1) Complex

In 2 ml of hot methylene chloride were dissolved 40 mg of 2,6-bis(methoxycarbonyl) TCNAQ and 10 mg (0.5 eq.) of TTF, and the solution was concentrated to obtain a green to black tar-like substance. The product was suspended in 3 ml of diethyl ether, followed by filtration. The filter cake was washed with diethyl ether to obtain 33 mg of the entitled complex as a green powder having a melting point of 238°–239° C. (decomp.).

Elementary Analysis for $C_{27}H_{14}N_4S_2O_4$: Calcd. (%): C 62.06; H 2.70; N 10.72; S 12.27; Found (%): C 61.71; H 2.63; N 10.86; S 11.89.

EXAMPLE 26

Preparation of 2,6-Dimethyl TCNAQ-Benzene Complex

In 2 ml of hot benzene was dissolved 50 mg of 2,6-dimethyl TCNAQ. The resulting solution was allowed to cool and filtered to obtain 55 mg of yellow flaky crystals. These crystals were labile and evaporated benzene at room temperature.

Figure 8:
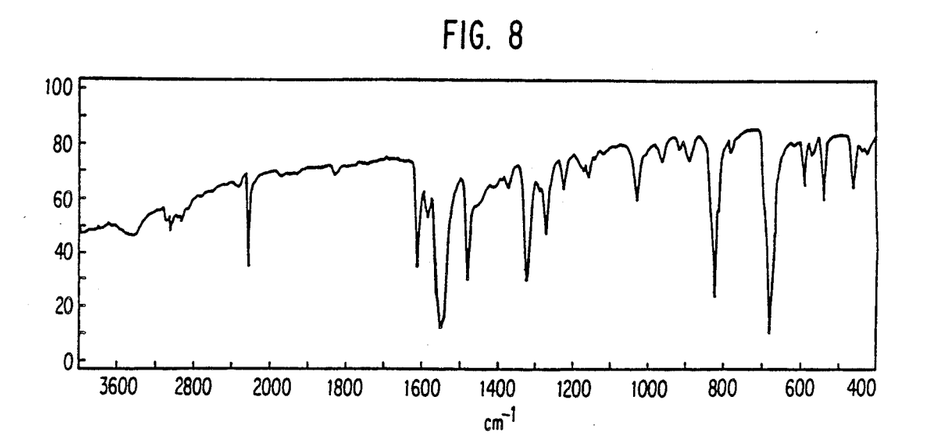

IR Spectrum (KBr): shown in FIG. 8.

EXAMPLE 27

Preparation of 2,6-Dimethyl TCNAQ-Naphthalene (1:1) Complex

In 1 ml of hot methylene chloride was dissolved 50 mg of 2,6-dimethyl TCNAQ, and 100 mg (large excess) of naphthalene was added to the solution. The solvent was removed by distillation under reduced pressure, and the residual orange tar-like substance was rubbed with a spatula to crystallize. The resulting crystal was suspended in 2 ml of carbon tetrachloride, followed by filtration. The filter cake was washed with carbon tetrachloride to obtain 36 mg of the entitled complex as a yellow powder having a melting point of 140°-220° C. (decomp.).

Elementary Analysis for $C_{32}H_{20}N_4$: Calcd. (%): C 83.46; H 4.38; N 12.17; Found (%): C 83.72; H 4.14; N 12.40.

EXAMPLE 28

Preparation of 2,6-Dimethyl TCNAQ-Phenanthrene (1:1) Complex

In 2 ml of hot methylene chloride was dissolved 50 mg of 2,6-dimethyl TCNAQ, and 54 mg (2 eq.) of phenanthrene was added thereto. The solvent was removed by distillation, and the residual orange tarlike substance was rubbed with a spatula to crystallize. The crystal was suspended in 3 ml of ethanol, followed by filtration. The filter cake was washed with ethanol to obtain 51 mg of the entitled complex as a yellow powder having a melting point of 259°-260° C. (decomp.)

Elementary Analysis for $C_{36}H_{22}N_4$: Calcd. (%): C 84.68; H 4.34; N 10.97; Found (%): C 83.90; H 4.23; N 9.92.

EXAMPLE 29

Preparation of 2,6-Dimethyl TCNAQ-Pyrene (2:1) Complex

In 2 ml of hot methylene chloride were dissolved 50 mg of 2,6-dimethyl TCNAQ and 61 mg (2 eq.) of pyrene, and the solvent was removed from the solution by distillation. The resulting vermilion tar-like substance was suspended in 2 ml of carbon tetrachloride, followed by filtration. The filter cake was washed with carbon tetrachloride to obtain 50 mg of the entitled complex as an orange powder having a melting point of 208°-209° C.

Elementary Analysis for $C_{30}H_{17}N_4$; Calcd. (%): C 83.12; H 3.95; N 12.92; Found (%): C 83.48; H 3.67; N 12.87.

EXAMPLE 30

Preparation of 2,6-Dimethyl TCNAQ-2,3,5,6-Tetramethyl-p-phenylenediamine (2:1) Complex In 2 ml of hot methylene chloride was dissolved 50 mg of 2,6-dimethyl TCNAQ, and 49 mg (2 eq.) of 2,3,5,6-tetramethyl-p-phenylenediamine was added thereto. The solution was concentrated to 1 ml, and the concentrate was allowed to cool and then filtered. The filter cake was washed with a large quantity of carbon tetrachloride to obtain 35 mg of the entitled complex as a green crystal having a melting point of 212°-226° C. (decomp.).

Figure 9:
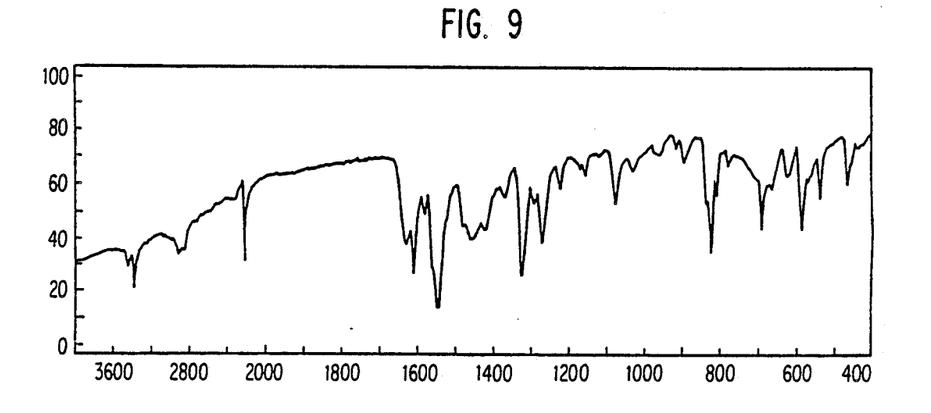

IR Spectrum (KBr): shown in FIG. 9.

Elementary Analysis for $C_{27}H_{20}N_5$: Calcd. (%): C 78.24; H 4.86; N 16.90; Found (%): C 78.42; H 4.72; N 16.86.

EXAMPLE 31

Preparation of 2,6-Dimethyl TCNAQ-TTF (1:1) Complex

In 2 ml of hot methylene chloride was dissolved 50 mg of 2,6-dimethyl TCNAQ, and 61 mg (2 eq.) of TTF was added to the solution. The solution was concentrated to 0.5 ml, and to the concentrate was added 2 ml of carbon tetrachloride. After allowing to cool, the mixture was filtered, and the filter cake was washed with carbon tetrachloride to obtain 75 mg of the entitled complex as a dark green needle-like crystal having a melting point of 185°-188° C. (decomp.).

Figure 10:
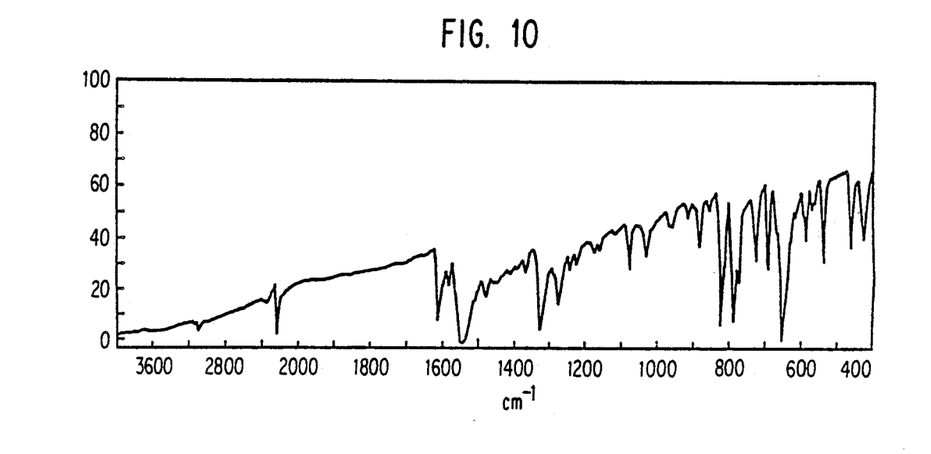

IR Spectrum (KBr): shown in FIG. 10.

Elementary Analysis for $C_{28}H_{16}N_4S_4$: Calcd. (%): C 62.66; H 3.00; N 10.44; S 23.90; Found (%): C 62.25; H 2.82; N 10.27; S 23.84.

EXAMPLE 32

Preparation of 2,7-Bis(methoxycarbonyl) TCNAQ-Benzene (1:1) Complex

In 100 ml of hot benzene was dissolved 917 mg of 2,7-bis(methoxycarbonyl) TCNAQ, and the solution was concentrated to 30 ml. To the concentrate was added 5 ml of hexane, followed by allowing to cool. The mixture was filtered to obtain 540 mg of the entitled complex as a yellow crystal having a melting point of 130°-145° C. (decomp.).

Elementary Analysis for $C_{30}H_{18}N_4O_4$: Calcd. (%): C 72.28; H 3.64; N 11.24; Found (%): C 72.49; H 3.50; N 11.08.

EXAMPLE 33

A solution containing 3 parts by weight of a polyester resin and 2 parts by weight of a bisazo pigment was coated on an aluminum plate to form a charge generating layer having a thickness of 2 μm. A solution containing 3 parts by weight of 2,6-dichloro TCNAQ as prepared in Example 1 and 2 parts by weight of a polycarbonate resin was coated thereon to form a charge transport layer having a thickness of 20 μm.

When the resulting photoreceptor was uniformly charged positively and then imagewise exposed to light, an electrostatic latent image having an electrostatic contrast of 550 V was formed. Upon development of the latent image, a clear copy image was obtained.

When the latent image formation was repeatedly carried out, the increase in residual potential was about 100 V.

EXAMPLE 34

The same procedure of Example 33 was repeated, except for using 2,6-bis(methoxycarbonyl) TCNAQ as prepared in Example 3 in place of the 2,6-dichloro TCNAQ. As a result, satisfactory copy images were obtained.

As described above, the TCNAQ derivative according to the present invention can be obtained easily through one reaction step without involving incorporation of impurities. Because of high purity, the trap sites produced when they are applied to electrophotography are markedly reduced so that the residual potential and changes thereof with time can be reduced. Therefore, the compounds according to the present invention are suitable for use in electrophotographic photoreceptors for high-speed copying which exhibit high electron mobility and are chargeable to both poralities.

While the invention has been described in detail with reference to specific embodiments thereof, it will be apparent to one skilled in the art that various changes and modifications can be made therein without departing from the spirit and scope thereof.

What is claimed is:

1. A tetracyanoanthraquinodimethane derivative represented by formula (I)

wherein R represents a dialkylamino group wherein the alkyl moiety is a lower alkyl group; and n is 1 and m represents 0 or 1 such that m+n is 1 or 2.

2. The tetracyanoanthraquinodimethane derivative according to claim 1, wherein said lower alkyl group has from 1 to 5 carbon atoms.

3. The tetracyanoanthraquinodimethane derivative according to claim 2, wherein said lower alkyl group has from 1 to 3 carbon atoms.

* * * * *